(12) United States Patent
Bock et al.

(10) Patent No.: US 8,440,856 B2
(45) Date of Patent: May 14, 2013

(54) METHOD FOR TREATING RESIDUES FROM THE PRODUCTION OF ISOCYANATES

(75) Inventors: Michael Bock, Ruppertsberg (DE); Martin Sesing, Waldsee (DE); Eckhard Stroefer, Mannheim (DE)

(73) Assignee: BASF SE, Ludwigshafen (DE)

( * ) Notice: Subject to any disclaimer, the term of this patent is extended or adjusted under 35 U.S.C. 154(b) by 316 days.

(21) Appl. No.: 12/936,080

(22) PCT Filed: Apr. 9, 2009

(86) PCT No.: PCT/EP2009/054287
§ 371 (c)(1),
(2), (4) Date: Oct. 1, 2010

(87) PCT Pub. No.: WO2009/127591
PCT Pub. Date: Oct. 22, 2009

(65) Prior Publication Data
US 2011/0021836 A1    Jan. 27, 2011

(30) Foreign Application Priority Data
Apr. 14, 2008 (EP) .................... 08154471

(51) Int. Cl.
*C07C 293/10* (2006.01)
*C07C 209/84* (2006.01)
*C07C 209/86* (2006.01)
*C07C 265/14* (2006.01)
*C07C 211/50* (2006.01)

(52) U.S. Cl.
USPC ............ 560/347; 560/352; 564/305; 564/463

(58) Field of Classification Search .................. 560/347, 560/352
See application file for complete search history.

(56) References Cited

U.S. PATENT DOCUMENTS

| 3,128,310 A | 4/1964 | Koch |
| 3,331,876 A | 7/1967 | Van Horn et al. |
| 4,091,009 A | 5/1978 | Cassata |
| 4,654,443 A | 3/1987 | Marks et al. |
| 6,673,960 B1 | 1/2004 | Schwarz et al. |
| 7,342,134 B2 | 3/2008 | Knoesche et al. |
| 2008/0146835 A1 | 6/2008 | Lorenz et al. |

FOREIGN PATENT DOCUMENTS

| DE | 1 962 598 | 7/1970 |
| DE | 27 03 313 | 8/1978 |
| DE | 29 42 678 | 5/1981 |
| EP | 1 706 370 | 10/2006 |
| EP | 1 935 877 | 6/2008 |
| JP | 58 201751 | 11/1983 |
| WO | 99 65868 | 12/1999 |
| WO | 2004 108656 | 12/2004 |
| WO | 2006 134137 | 12/2006 |

OTHER PUBLICATIONS

U.S. Appl. No. 13/266,049, filed Oct. 24, 2011, Stroefer, et al.
International Search Report issued Oct. 30, 2009 in PCT/EP09/054287 filed Apr. 9, 2009.
U.S. Appl. No. 13/380,680, filed Dec. 23, 2011, Schelling, et al.
International Preliminary Report on Patentability issued Jan. 20, 2011 in Application No. PCT/EP2009/054287 (English Translation).
"Process Technology I (Basic Operations)", Ullmans Encyclopedia of Technical Chemistry, 4th revised and enlarged edition, vol. 2. 1972, pp. 282-300 (With English Translation and Translator's Report/Comments).
U.S. Appl. No. 13/125,895, filed Apr. 25, 2011, Geissler, et al.

*Primary Examiner* — Brian J Davis
(74) *Attorney, Agent, or Firm* — Oblon, Spivak, McClelland, Maier & Neustadt, L.L.P.

(57) ABSTRACT

This invention relates to a process for working up residues from production of isocyanates. This process involves hydrolyzing residues from production of at least one isocyanate with water to form a hydrolysis product, and processing the hydrolysis product within an extruder or a kneader having a heat transfer surface, to form a mixed product containing at least one amine and water. The amine and the water are separated from the mixed product to form an amine/water mixture, which is then separated to obtain the water and the amine. The process may also involve separating all or part of the water from the hydrolysis, or separating part of the amine from the hydrolysis, prior to the processing of the hydrolysis product.

20 Claims, No Drawings

METHOD FOR TREATING RESIDUES FROM THE PRODUCTION OF ISOCYANATES

CROSS-REFERENCE TO RELATED APPLICATIONS

This application is a National Stage of PCT/EP09/54287 filed Apr. 9, 2009. This application is based upon and claims the benefit of priority from European Patent Application No. 08154471.0 filed Apr. 14, 2008.

BACKGROUND OF THE INVENTION

The invention relates to a process for the work-up of isocyanate adducts such as polyurethanes, residues from isocyanate production, in particular distillation residues from the preparation of tolylene diisocyanate (TDI) or hexamethylene diisocyanate (HDI).

Isocyanate adducts are obtained in large quantities as waste material in industry. Examples are polyurethane foams, here, for example, production scrap or foams from redundant appliances, motor vehicles or furniture.

A further group of isocyanate adducts is made up of production wastes, in particular distillation residues from the preparation of polyisocyanates, in particular tolylene diisocyanate (TDI) or hexamethylene diisocyanate (HDI). Particularly in the preparation of TDI, one of the most used polyisocyanates, a large amount of residues is obtained.

TDI is used in large quantities for producing polyurethanes, in particular flexible polyurethane foams. The preparation of TDI is usually carried out by reacting tolylenediamine (TDA) with phosgene. This process has been known for a long time and is widely described in the literature.

For this purpose, the TDA is usually reacted with phosgene in a conventional two-stage phosgenation.

At the end of the synthesis, there is usually a distillation step in which TDI is separated off from high-boiling by-products. For process engineering reasons, for example to ensure the pumpability of the residue, the residue can still comprise up to 70%, preferably up to 50%, particularly preferably up to 30%, of TDI. Thus, there is a considerable economic incentive to make use of the materials in this residue in the case of present-day "world scale plants" having an annual capacity of up to several hundred thousand metric tons.

One possibility which is frequently employed to recover at least part of the TDI comprised in the distillation residue is to remove more of the TDI from the residue, for example by means of an extruder. Suitable apparatuses are, for example, List dryers. These are specific paddle dryers from List which are frequently used in isocyanate production. The amount of TDI in the distillation residue can be significantly reduced in this way. However, this process also produces a generally solid residue, as a result of which the yield of the process is reduced. This residue has hitherto usually been burnt.

An alternative way of utilizing the distillation residues is to make use of the materials there. Various processes are known for this.

One such possibility for utilization is reaction of the residue with water, known as hydrolysis. Such processes are widely described. Hydrolysis of the residue is promoted by bases or acids. Amines also promote hydrolysis. Hydrolysis can be used for denaturing the TDI distillation residue, as described, for example, in U.S. Pat. No. 4,091,009. A further possibility is the recovery of TDA which can then be reacted again with phosgene to form TDI. Such processes are described, for example, in DE-A 29 42 678, JP-A 5 8201 751 and DE-A 19 62 598.

DE-A 27 03 313 describes a hydrolysis process which can be carried out either batchwise in an autoclave or continuously in a tube reactor. The hydrolysis of the solid TDI residue is carried out using aqueous ammonia solution, solutions of primary or secondary amines in water or aqueous TDA solution.

U.S. Pat. No. 4,654,443 describes a hydrolysis process in which the TDI residue is reacted with TDA to form a solid in a first process step and this intermediate is hydrolyzed with water in a second step.

The hydrolysis enables a large part of the products of value comprised in the residue to be recovered. However, complete transformation is not possible in the known processes, so that products of value are still lost.

WO 2006/134137 describes a process for the work-up of isocyanate residues, in which monomeric isocyanate is firstly separated off from the residue in a List dryer and the residue obtained is treated with ammonia. In this process, too, there is only incomplete recovery of the materials of value, and in addition ammonia is difficult to handle.

It was an object of the present invention to develop a process for the work-up of residues from the production of isocyanates, in which a higher yield can be achieved and which is easy to manage.

BRIEF SUMMARY OF THE INVENTION

The object has surprisingly been able to be achieved by firstly subjecting the residue to hydrolysis and then introducing the reaction product of the hydrolysis into a mixer having a heat transfer surface, preferably an extruder or kneader.

The invention accordingly provides a process for the work-up of residues from the production of isocyanates, which comprises the steps:

a) hydrolysis of the residues by means of water,
b) introduction of the reaction product from step a) into a mixer having a heat transfer surface, preferably a kneader or an extruder,
c) separation of amine and water from the output from step b),
d) separation of water and amine.

DETAILED DESCRIPTION OF THE INVENTION

It is possible here to separate all or part of the water from the reaction product from step a) between steps a) and b).

Furthermore, it is possible to separate part of the amine formed in step a) from the reaction product between steps a) and b).

Separation of part of the products from the reaction mixture enables the amount of product treated in step b) to be reduced, thereby making it possible to make the reaction apparatuses used in step b) smaller.

The amount of amine and/or water separated off should be only such amount that the mixture remains pumpable and can be transported without problems through the apparatus used in step b). The viscosity of the mixture should therefore typically be less than 500 mPas.

In a preferred embodiment, step a), step b) or both steps can be carried out in the presence of a base. This base is different from the amine which is the target product of the process of the invention.

The base in step a) should have a base strength which is greater than that of the amine which is the target product of the process of the invention.

The base strength of the base used in step b) should also be greater than that of the amine which is the target product of the process of the invention. If, in this embodiment of the process of the invention, a base has been used in step a), the base strength of the base used in step b) should be greater than that of all bases used in step a).

The bases used in steps a) and b) can be basic oxides or hydroxides of metals. They are preferably oxides or hydroxides of alkali metals and/or alkaline earth metals, in particular hydroxides of alkali metals and/or alkaline earth metals. Particular preference is given to using potassium hydroxide or sodium hydroxide as solid or concentrated solutions.

In a further embodiment of the invention, nitrogen-comprising compounds are used as bases. These are preferably selected from the group consisting of primary, secondary and tertiary amines, ammonia and heterocyclic nitrogen compounds such as imidazoles.

The base can be added in the two steps either before or during the reaction.

In a particular embodiment of the process of the invention, mixtures comprising amino groups from distillation bottoms from an amine production process are used as base, either alone or in combination with further bases from among those mentioned. These distillation bottoms are preferably residues from the amines used for the preparation of the isocyanates from which the residues used in step a) originate. These amine residues are obtained, in particular, in the work-up of the amines by distillation, as described, for example, in EP 1 706 370. However, other amine-comprising streams are also possible. The amine residues are preferably used in combination with other bases. If the basicity of the amine residues is lower than that of the amine formed in the hydrolysis, a stronger base, preferably from the abovementioned group, is present.

It is usual to introduce from 0.1 to 15 mol of base/kg of hydrolysis residue into the kneader or extruder. Particular preference is given to introducing from 0.2 to 5 mol of base/kg of hydrolysis residue into the kneader or extruder.

The process is preferably configured so that the strongest base is used last and organic base is used before inorganic base.

Removal of the bases from the output from the process is not necessary and is therefore not carried out.

The hydrolysis can be carried out either batchwise or continuously. The decision regarding this depends first and foremost on the amount of the residues obtained in the respective isocyanate production process.

The reaction of the isocyanate adducts with water is preferably carried out at a temperature in the range from 100 to 500° C., preferably from 100 to 400° C., particularly preferably from 100 to 250° C., and a pressure in the range from 20 to 500 bar, preferably from 30 to 400 bar and particularly preferably from 30 to 380 bar.

The water has to be present in an at least equimolar amount based on the bond to be cleaved. Preference is given to using it in a molar excess of at least 10%. Since the composition of the residues depends strongly on the reaction conditions in the production process and cannot be determined accurately by analysis, the amount of water is in the following reported in % by weight. The proportion of water among the starting components of the process of the invention is preferably in the range from 10% by weight to 90% by weight, preferably from 30% to 70% by weight, based on the reaction mixture of the hydrolysis.

The reaction product of step a) is usually taken continuously from the reactor and worked up continuously. In the preferred solvent-free process, the reaction product consists of a single phase when the reaction is complete.

The reaction can be carried out in tube reactors, in vessels or in cascades of stirred vessels. The residence time is preferably in the range from 30 seconds to 7 hours, preferably in the range from 10 minutes to 5 hours.

The reaction product from step a) is, if appropriate after the above-described separation of water and amine, transferred to the mixer having a heat transfer surface, preferably a kneader or extruder, of step b). Further reduction of the residue is effected there.

As extruder or kneader, it is possible to use single-screw, twin-screw, ring, multiscrew or planetary-gear extruders, single-screw or twin-screw kneaders or paddle dryers.

Preference is given to single-screw or twin-screw kneaders as are produced by the companies List and Buss-SMS. Compounding extruders from Coperion are also well suited.

The reaction with the base in the mixer having a heat transfer surface, in particular the extruder or kneader, is carried out at a reduced pressure of from 20 to 900 mbar and at from 100 to 250° C. The reaction is preferably carried out at from 20 to 100 mbar and from 150 to 245° C. The residence time of the product is from 10 minutes to 5 hours.

The amine and, if still present, the water is/are separated off from the reaction product from step b). This can be effected, for example, by distillation. The amine or amine/water mixture which has been separated off can, if necessary, be passed to a further work-up. This comprises, for example, removal of the remaining water and of other volatile constituents. This is preferably effected by distillation.

The worked-up amine can be reused in the process for the preparation of isocyanates.

The residue remaining after amine and water have been separated off is discharged and can be deposited in a landfill or burnt.

The residues from the production of isocyanates, in particular tolylene diisocyanate (TDI) and hexamethylene diisocyanate (MDI), can be worked up by the process of the invention. The yield of the work-up can be increased further by means of the process of the invention.

The process is illustrated by the following examples.

Example 1

5 kg of a tar from the hydrolysis of TDI residues were introduced together with 0.7 kg of potassium hydroxide solution (50% strength by weight) into a closed kneader. The reaction mixture was kneaded at 230° C. for 3 hours. The reaction product mixture comprised 53% by weight of TDA. At the end of the process, the mixture of TDA and water was distilled off from the kneader at 40 mbar and 230° C. and subsequently separated into TDA and water. The TDA obtained in this way could, in a continuous process, be fed back into a phosgenation.

Example 2

5 kg of a tar from the hydrolysis of TDI residues, 0.7 kg of potassium hydroxide solution (50% strength by weight) and 5 kg of a high-boiling TDA residue from the work-up after the hydrogenation of DNT to TDA were introduced into a closed kneader. The reaction mixture was kneaded at 230° C. for 3 hours. At the end of the process, the mixture of TDA and water was distilled off from the kneader at 40 mbar and 230° C. and subsequently separated into TDA and water. The TDA obtained in this way could, in a continuous process, be fed back into a phosgenation.

Example 3

5 kg of a tar from the hydrolysis of TDI residues, 0.7 kg of potassium hydroxide solution (50% strength by weight) and 5 kg of a high-boiling amine residue from alkylamine production were introduced into a closed kneader. The reaction mixture was kneaded at 230° C. for 3 hours. At the end of the process, the mixture of TDA and water was distilled off from the kneader at 40 mbar and 230° C. and subsequently separated into TDA and water. The TDA obtained in this way could, in a continuous process, be fed back into a phosgenation.

The invention claimed is:

1. A process for working up residues from production of an isocyanate, the process comprising:
   a) hydrolyzing residues from production of at least one isocyanate with water to form a hydrolysis product;
   b) processing the hydrolysis product within an extruder or a kneader, each having a heat transfer surface, to form a mixed product comprising at least one amine and water;
   c) separating the at least one amine and the water from the mixed product, to form an amine/water mixture; and
   d) separating the amine/water mixture to obtain the water and the at least one amine.

2. The process according to claim 1, wherein the hydrolyzing a) occurs in the presence of a base a) whose basicity is greater than that of amine formed in the hydrolyzing a).

3. The process according to claim 1, wherein the processing b) occurs in the presence of a base b) whose basicity is greater than that of all bases present in the hydrolyzing a).

4. The process according to claim 2, wherein the base a) is at least one selected from the group consisting of an oxide of an alkali metal, a hydroxide of an alkali metal, an oxide of an alkaline earth metal, and a hydroxide of an alkaline earth metal.

5. The process according to claim 2, wherein the base a) is at least one selected from the group consisting of a hydroxide of an alkali metal and a hydroxide of an alkaline earth metal.

6. The process according to claim 2, wherein the base a) is a nitrogen-comprising compound.

7. The process according to claim 6, wherein the nitrogen-comprising compound is at least one selected from the group consisting of a primary amine, a secondary amine, a tertiary amine, ammonia and a heterocyclic nitrogen compound.

8. The process according to claim 1, comprising processing a) the hydrolysis product within a single-screw, twin-screw, ring, multiscrew or planetary-gear extruder, or a single-screw or twin-screw kneader or paddle dryer, each having a heat transfer surface.

9. A process for working up residues from production of an isocyanate, the process comprising:
   a) hydrolyzing residues from production of at least one isocyanate, and separating part or all of water from the hydrolyzing, to form a hydrolysis product;
   b) processing the hydrolysis product within an extruder or a kneader, each having a heat transfer surface, to form a mixed product comprising at least one amine and optionally water;
   c) separating the at least one amine and the water, if still present, from the mixed product to form a separated product comprising the at least one amine and optionally the water; and
   d) optionally separating the separated product to obtain the water and the at least one amine.

10. A process for working up residues from production of an isocyanate, the process comprising:
    a) hydrolyzing residues from production of at least one isocyanate, and separating part of amine formed in the hydrolyzing, to form a hydrolysis product;
    b) processing the hydrolysis product within an extruder or a kneader, each having a heat transfer surface, to form a mixed product comprising at least one remaining amine and water;
    c) separating the at least one remaining amine and the water from the mixed product to form an amine/water mixture; and
    d) separating the amine/water mixture to obtain the water and the at least one remaining amine.

11. The process according to claim 2, wherein the base a) is at least one mixture comprising amino groups from distillation bottoms from an amine production process.

12. The process according to claim 3, wherein the processing b) occurs in the presence of a base b) whose basicity is greater than that of all bases present in the hydrolyzing a), and greater than that of amine formed in the hydrolyzing a).

13. The process according to claim 3, wherein the base b) is at least one selected from the group consisting of an oxide of an alkali metal, a hydroxide of an alkali metal, an oxide of an alkaline earth metal, and a hydroxide of an alkaline earth metal.

14. The process according to claim 3, wherein the base b) is at least one selected from the group consisting of a hydroxide of an alkali metal and a hydroxide of an alkaline earth metal.

15. The process according to claim 3, wherein the base b) is a nitrogen-comprising compound.

16. The process according to claim 15, wherein the nitrogen-comprising compound is at least one selected from the group consisting of a primary amine, a secondary amine, a tertiary amine, ammonia and a heterocyclic nitrogen compound.

17. The process according to claim 1, comprising processing b) the hydrolysis product within a single-screw or twin-screw kneader having a heat transfer surface.

18. The process according to claim 1, comprising processing b) the hydrolysis product within a paddle dryer comprising a heat transfer surface.

19. The process according to claim 3, wherein the base b) is at least one mixture comprising amino groups from distillation bottoms from an amine production process.

20. The process according to claim 2, wherein the processing b) occurs in the presence of a base b) whose basicity is greater than that of all bases present in the hydrolyzing a).

* * * * *